(12) United States Patent
Masters et al.

(10) Patent No.: US 12,324,702 B2
(45) Date of Patent: Jun. 10, 2025

(54) ULTRASONIC CATHETER

(71) Applicant: Boston Scientific Scimed, Inc., Maple Grove, MN (US)

(72) Inventors: Donald Masters, Sylmar, CA (US); Jesus Andres Lopez, Bloomington, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 242 days.

(21) Appl. No.: 18/052,926

(22) Filed: Nov. 6, 2022

(65) Prior Publication Data

US 2024/0148356 A1     May 9, 2024

(51) Int. Cl.
*A61B 8/12*     (2006.01)
*A61B 8/00*     (2006.01)

(52) U.S. Cl.
CPC ............ *A61B 8/12* (2013.01); *A61B 8/445* (2013.01)

(58) Field of Classification Search
CPC ......... A61B 8/12; A61B 8/445; A61B 8/0883; A61B 8/4483; A61B 8/4488; B06B 2201/55; B06B 2201/76; B06B 1/0215; G01H 3/00
See application file for complete search history.

(56) References Cited

U.S. PATENT DOCUMENTS

| | | | |
|---|---|---|---|
| 2010/0168583 A1* | 7/2010 | Dausch | B06B 1/0622 600/466 |
| 2013/0261467 A1* | 10/2013 | Dausch | A61B 8/12 29/25.35 |
| 2015/0305708 A1* | 10/2015 | Stigall | A61B 8/12 600/467 |
| 2017/0252777 A1* | 9/2017 | Kidwell, Jr. | H10N 30/074 |
| 2017/0290562 A1* | 10/2017 | Corl | A61B 8/4461 |
| 2018/0140278 A1* | 5/2018 | Bromberg | A61B 8/4494 |
| 2019/0357879 A1* | 11/2019 | Corl | A61B 8/54 |
| 2022/0346750 A1* | 11/2022 | Robinson | A61B 8/12 |

OTHER PUBLICATIONS

International Search Report and Written Opinion received for PCT Patent Application No. PCT/US23/78696, mailed on Mar. 4, 2024, 6 pages.

* cited by examiner

*Primary Examiner* — Hien N Nguyen
(74) *Attorney, Agent, or Firm* — Nelson Mullins Riley & Scarborough LLP

(57) ABSTRACT

An ultrasonic catheter is disclosed. The ultrasonic catheter comprises a micro-electromechanical (MEMS) based Piezoelectric Micromachined Ultrasonic Transducer (pMUT) array disposed within a distal end of a body. The ultrasonic catheter further comprises a plurality of electronic flex circuits, connected at one end to a handle connector and at other end to a first layer of AIC. The handle connector passes ultrasound signals to the distal end via the plurality of electronic flex circuits. Further, a distal pMUT interposer is disposed between the first layer and a second layer of AIC, with InvisiVia connections. The InvisiVia connection is configured to bring the electronic flex circuit from one side of the distal pMUT interposer to the other. Further, the MEMS based pMUT array sends a pressure wave and receives a returning pressure wave echo via the InvisiVia connections of the distal pMUT interposer.

18 Claims, 7 Drawing Sheets

ULTRASONIC CATHETER

FIELD OF THE DISCLOSURE

The present disclosure relates generally to the field of ultrasonic catheter. More particularly, some embodiments relate to ultrasonic catheters having a distal piezoelectric micromachined transducer (pMUT) interposer referred as "InvisiVia" connections, for transmitting and receiving acoustic pulse information.

BACKGROUND OF THE DISCLOSURE

Use of catheter-based structural and electrophysiological procedures have recently expanded to more complex scenarios, in which an accurate definition of variable individual cardiac anatomy is a key to obtain optimal results. Intracardiac echocardiography (ICE) is a unique imaging modality for high-resolution real-time visualization of cardiac structures, continuous monitoring of catheter location within the heart, and early recognition of procedural complications, such as pericardial effusion or thrombus formation. Further, ICE imaging modality includes additional benefits, such as excellent patient tolerance, reduction of fluoroscopy time, and elimination of need for general anaesthesia or second operator. Currently, ICE imaging modality has largely replaced trans-oesophageal echocardiography as ideal imaging modality for guiding certain procedures, such as atrial septal defect closure and catheter ablation of cardiac arrhythmias, and has an emerging role in others, including mitral valvuloplasty, transcatheter aortic valve replacement, and left atrial appendage closure.

ICE catheters involve interconnection of multidimensional transducer arrays with electronics. A technological challenge for the multidimensional transducer arrays is to create a secure and stable interconnection between an acoustic array and associated echoes. There are hundreds of different elements distributed in two dimensions which require interconnection along z-axis (in depth or range) for some elements surrounded by other elements. Since the elements are small in size, there is a limited space for a separate electrical connection to each element. There are a variety of approaches to provide interconnection for the multidimensional transducer array, such as, a chip-on-array, a frame-based approach, and a multi-layered flex. In the chip-on-array, the acoustic array is built-up directly on an application specific integrated circuit (ASIC) chip's input/output (I/O). Due to possible failure in the acoustic array a very low process yield may result.

In the frame-based approach, the array is divided into few sections. Each section has a solid metal frame. Flex circuits bent around the metal frames redistribute as many signals as a number of acoustic elements from the acoustic elements to ASICs placed on the flex circuits. However, signal routing of the frame-based approach is more complicated than chip-on-array, which results in higher electrical parasitic. In the multi-layered flex approach, stacks may be divided into flex circuits to route the signals for elements without any aperture sectioning. However, these approaches either end up in an expensive structure of interconnection for the multidimensional transducer array, or there is a certain undesired leakage to bulk section substrate of the transducer array.

Therefore, there is a need for an improved ultrasonic catheter with a high-density flexible circuit having electrical insulated interconnects to enable highly repeatable and stable transmission of signals.

SUMMARY OF THE DISCLOSURE

By way of introduction, the preferred embodiments described below include an easy-to-use ultrasonic catheter is disclosed. The ultrasonic catheter comprises a body having a longitudinal axis, a proximal end, and a distal end. Further, the ultrasonic catheter comprises a micro-electromechanical (MEMS) based Piezoelectric Micromachined Ultrasonic Transducer (pMUT) array disposed within the distal end of the body. The ultrasonic catheter further comprises a plurality of electronic flex circuits, connected at one end to a handle connector and at other end to a first layer of Adhesive Interconnect (AIC). The handle connector passes ultrasound signals to the distal end via the plurality of electronic flex circuits. Further, the ultrasonic catheter comprises a distal pMUT interposer disposed between the Flex circuit layer and a second layer of Anisotropic Conductive Film (ACF) or similar AIC, with what we refer to as "InvisiVia" connections.

The InvisiVia feature provides a conductive interconnect from one side of the flexible circuit to the other side of the flexible circuit. Thus, the InvisiVia creates a flat and planar interconnect from the flex circuitry to the flex bonding pads by way of a thermocompression electrical connection. Further, the MEMS based pMUT array receives an electronic pulse through the flex circuit and through the conductive InvisiVia to the pMUT, generating a pressure wave and the returning pressure wave stimulates the pMUT creating a return an electrical signal through the conductive InvisiVia connections of the distal pMUT interposer.

It can be noted that the distal pMUT interposer corresponds to an ultra-high-density interconnect (UHDI) flexible circuit interposer connected to the MEMS based pMUT array through an UHDI pad array. The UHDI pad array is connected to the MEMS based pMUT array through a use of near zero evidence interfacial via. Further, the use of conductive InvisiVia connections creates a higher percentage of flat and planar conductive surface area on the UHDI pad. In one embodiment, the InvisiVia connections creates a flat and planner interconnect diameter of less than 15 microns. Thus, the use of InvisiVia connections eliminates a potential for undesired surface topography, creates a larger percentage of conductive surface are and helps prevent leakage to bulk silicon substrate of the MEMS based pMUT array.

Other features and aspects of this disclosure will be apparent from the following description and the accompanying drawings.

BRIEF DESCRIPTION OF THE DRAWINGS

Various embodiments will hereinafter be described in accordance with the appended drawings, which are provided to illustrate and not to limit the scope of the disclosure in any manner, wherein similar designations denote similar elements, and in which.

DETAILED DESCRIPTION

The components of the embodiments as generally described and illustrated in the figures herein can be arranged and designed in a wide variety of different configurations. Thus, the following more detailed description of various embodiments, as represented in the figures, is not intended to limit the scope of the present disclosure but is merely representative of various embodiments. While various aspects of the embodiments are presented in drawings, the drawings are not necessarily drawn to scale unless specifically indicated.

Some embodiments of this disclosure, illustrating all its features, will now be discussed in detail. The words "comprising," "having," "containing," and "including," and other forms thereof, are intended to be equivalent in meaning and be open-ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred systems, and methods are now described. The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Embodiments of the present disclosure will be described more fully hereinafter with reference to the accompanying drawings in which like numerals represent like elements throughout the several figures, and in which example embodiments are shown. Embodiments of the present disclosure may, however, be embodied in alternative forms and should not be construed as being limited to the embodiments set forth herein. The examples set forth herein are non-limiting examples and are merely examples among other possible examples.

Figure 1:
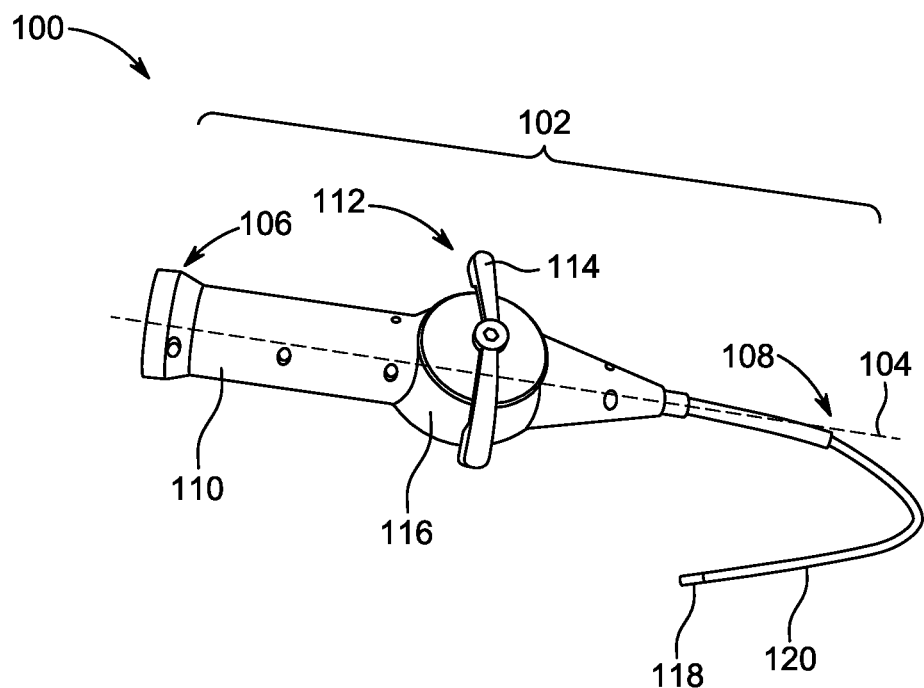
FIG. 1 illustrates a perspective view of an ultrasonic catheter, according to an embodiment of the present disclosure.

FIG. 1 illustrates a perspective view of an ultrasonic catheter 100, according to an embodiment of the present disclosure. The ultrasonic catheter 100 may comprise a body 102 having a longitudinal axis 104, a proximal end 106, and a distal end 108, a handle assembly 110, a steering control unit 112 having a steering handle 114 and a housing 116, and a distal tip 118.

The handle assembly 110 may be positioned between the proximal end 106 and the distal end 108 of the ultrasonic catheter 100. Further, the steering control unit 112 may be positioned within the handle assembly 110. The steering control unit 112 may be provided for articulating the distal tip 118 of the ultrasonic catheter 100. Further, the steering control unit 112 may align face of a micro-electromechanical (MEMS) based Piezoelectric Micromachined Ultrasonic Transducer (pMUT) array (not shown) towards different view including an anterior position and a posterior position inside the heart. Further, the steering control unit 112 may comprise the steering handle 114 and the housing 116 enclosing an actuator (not shown) and a steering hub (not shown). It can be noted that an internal friction occurs between the actuator and the steering hub, and between the actuator and the housing 116, which causes the ultrasonic catheter 100 to retain its adjusted configuration without operator attention. Further, the steering handle 114 may be rotated to facilitate positioning of the distal tip 118 of the ultrasonic catheter 100.

In one embodiment, the steering handle 114 may be rotated to position the distal tip 118 inside a chamber of a heart of a patient. In one embodiment, the steering control unit 112 may comprise a set of steering lines controlled by the steering control unit 112 to articulate multi-directionally a distal segment of the ultrasonic catheter 100 when placed inside the heart. Further, the ultrasonic catheter 100 may be disposed within the chamber of the heart of a patient and coupled to an imaging system (not shown) using a dongle cable (not shown) for displaying two-dimensional (2D) or three-dimensional (3D) images of the chamber of the heart using ultrasound waves and acoustic pulses.

Further, the ultrasonic catheter 100 may be used to perform electrophysiology (EP). The ultrasonic catheter 100 may be used for diagnosis and/or treatment in combination with another imaging modality, such as an x-ray, fluoroscopy, magnetic resonance, computed tomography, or optical system. Both imaging modalities may scan a patient for generating images to assist a physician. The data from the different modalities may be aligned by locating markers with a known spatial relationship to the ultrasound scan in the images of the other modality. In other embodiments, the ultrasonic catheter 100 may be a flexible cylindrical section without the markers and/or without another imaging modality. In one embodiment, the ultrasonic catheter 100 may utilize a microelectromechanical (MEMS) system defined as piezoelectric micro-machined ultrasound transducer (pMUT) or other types of MEMS transducers, interconnected using matched flexible circuits. In one embodiment, the ultrasonic catheter 100 may correspond to an intracardiac echocardiography (ICE) MEMS ultrasonic catheter utilizing a high-density flexible circuit for all transmission and electrical interconnects. It can be noted that the use of the high-density flexible circuits may enable highly repeatable and stable transmission and return signals. Further, the high-density flexible circuit transmission lines may transmit electrical energy from one end to another end of the ultrasonic catheter 100.

Further, the ultrasonic catheter 100 may comprise a catheter shaft 120. The catheter shaft 120 may be coupled to the handle assembly 110 at one end and to the distal tip 118 of the ultrasonic catheter 100 at the other end. Further, the catheter shaft 120 may enclose an electronic flexible circuit (not shown) and a plurality of steering cables (not shown). In one embodiment, the electronic flex circuit may be referred to as flexible cables. It can be noted that the electronic flex circuit may be bend or tilt towards the anterior position and/or posterior position inside the chamber of the heart. In one embodiment, the electronic flex circuit may comprise a strand, wire, and/or thread, and is preferably made from a low profile, durable, non-elastic, and non-conducting material. In one embodiment, steering cables or steering wires may be made from stainless steel. In another embodiment, the steering cables may be made of synthetic materials, such as nylon or similar synthetic fibres, or plastics material, such as urethane, Teflon®, Kynar®, Kevlar®, polyethylene, multi-stranded nylon, or gel-spun polyethylene fibres. For example, the steering cables may be a multi-stranded Spectra® brand nylon line sold as Spiderwire® fishing line (10 lbs. test).

The ultrasonic catheter 100 may be provided to transmit ultrasound signals inside the chamber of the heart of the patient. In one embodiment, the ultrasonic catheter 100 may be a flexible elongate member with the body 102 having the catheter shaft 120 at one end and the handle assembly 110 at another end. In one embodiment, the distal tip 118 of the ultrasonic catheter 100 may be coated with an insulating material. Further, the insulating material may be disposed at the distal end 108 over an imaging window (not shown), to prevent electrical breakdown and leakage of electrical signals from the ultrasonic catheter 100. The insulating material may be a copolymer material such as, but not limited to, polyether block amide (PEBA, for example, available under the trade name PEBAX®), and a thermoplastic elastomer (TPE). In one embodiment, the insulating material provides a low loss acoustic window. It can be noted that the insulating material provides a low loss path of acoustic echo when the ultrasonic catheter 100 is inserted inside the heart of the patient.

Figure 2:
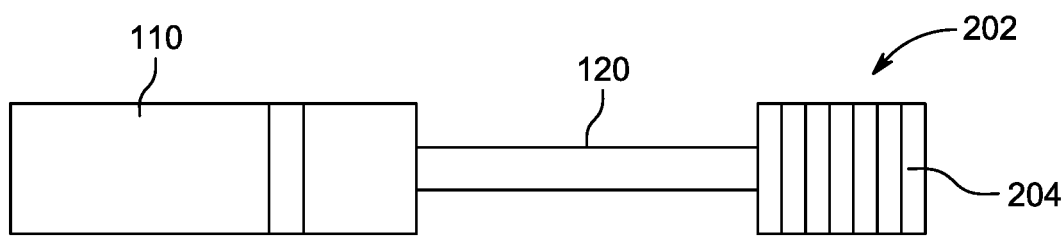
FIG. 2 illustrates a schematic diagram of a front view of the ultrasonic catheter, according to an embodiment of the present disclosure.

FIG. 2 illustrates a schematic diagram of the ultrasonic catheter 100, according to an embodiment of the present disclosure. FIG. 2 is described in conjunction with FIG. 1.

The ultrasonic catheter 100 may comprise a micro-electromechanical (MEMS) based Piezoelectric Micromachined Ultrasonic Transducer (pMUT) array 202 and a substrate 204. The MEMS based pMUT array 202 may be disposed over the substrate 204 towards the distal end 108 of the ultrasonic catheter 100. Further, the MEMS based pMUT array 202 may be disposed within the distal tip 118 of the ultrasonic catheter 100.

The catheter shaft 120 may be coupled between the handle assembly 110 via a distal pMUT interposer (not shown) and the MEMS based pMUT array 202. The electronic flex circuit inside the catheter shaft 120 may receive the at least one signal from the MEMS based pMUT array 202 and the received signal may be communicated back to an imaging device (not shown). Further, the MEMS based pMUT array 202 may send pressure waves to a target and receive a returning pressure wave echo from the target. In one embodiment, the target may be inside the chamber of heart of the patient. The MEMS based pMUT array 202 may transmit the received pressure wave echo back to the imaging device via the electronic flex circuit to further analyze the pressure wave echo for image generation. The MEMS based pMUT array 202 comprises a plurality of MEMS based pMUT array elements (not shown) arranged on the substrate 204.

In one embodiment, the ultrasonic catheter 100 may employ MEMS based pMUT array 202 with bulk piezoelectric transducer (PZT), piezoelectric micro machined (PMUT) transducer or capacitor micro machined transducer (CMUT) array for introduction through subclavian access for lead implantation for pacemaker, defilibulator, and structural heart implantation and other cardiac procedures.

Figure 3:
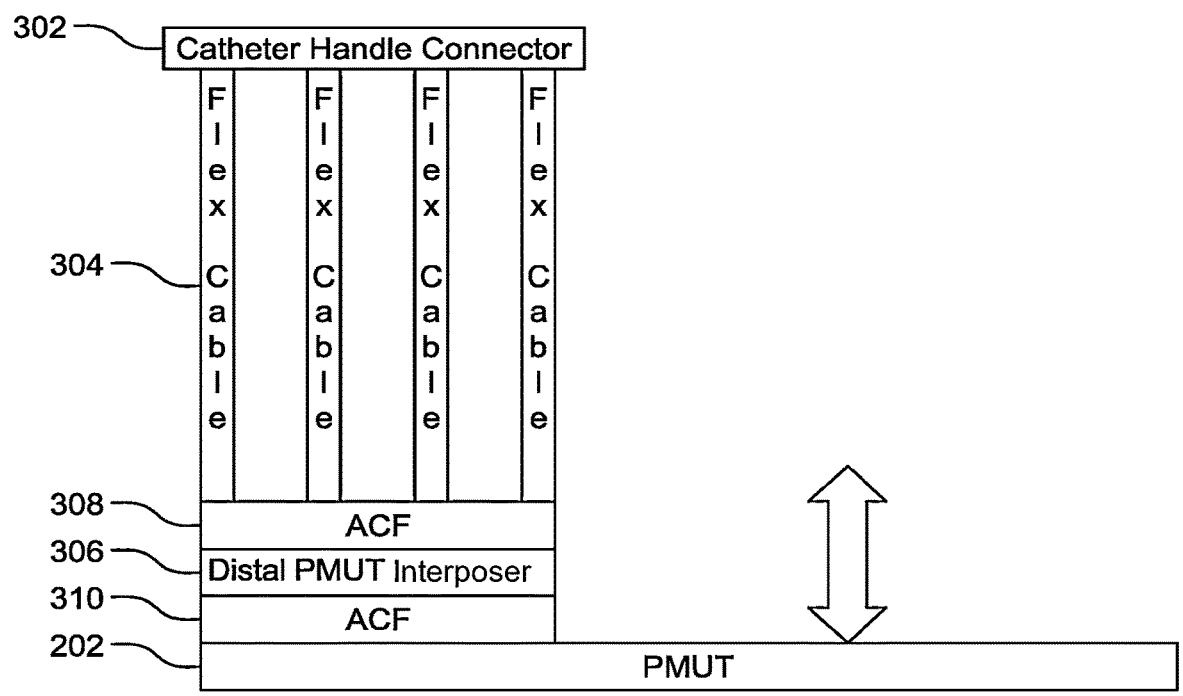
FIG. 3 illustrates an interconnect diagram showing a side view stack-up of electronic flex connection to a micro-electromechanical (MEMS) based Piezoelectric Micromachined Ultrasonic Transducer (pMUT) array or other type of Transducer, through a layer or layers of Adhesive Interconnect (AIC) such as Anisotropic Conductor Film (ACF), Anisotropic Conductive Paste (ACP), or similar Anisotropic Conductive Adhesives (ACAs) or through Electrically Conductive Adhesives (ECAs) or other such conductive adhesive, according to an embodiment of the present disclosure.

FIG. 3 illustrates an interconnect diagram showing a side view stackup of electronic flex connection to a microelectromechanical (MEMS) based Piezoelectric Micromachined Ultrasonic Transducer (pMUT) array, through layers of AIC, according to an embodiment of the present disclosure. FIG. 3 is described in conjunction with FIGS. 1 and 2.

Referring to FIG. 3, a compression connection is made among a catheter handle connector 302, a plurality of electronic flex circuits 304, the MEMS based pMUT array 202, and a distal pMUT interposer 306, using a first layer of AIC 308 and a second layer of AIC 310. The AIC may be made of a material selected from a group of materials of Anisotropic Conductor Film (ACF), anisotropic conductive paste (ACP), or similar anisotropic conductive adhesives (ACAs) or through Electrically Conductive Adhesives (ECAs) or other such conductive adhesive. The first layer of AIC 308 and the second layer of AIC 310 may sandwich the distal pMUT interposer 306 and create the compression connection between the plurality of electronic flex circuits 304 and the distal pMUT interposer 306. Further, the first layer of AIC 308 may be coupled to the catheter handle connector 302 via the plurality of electronic flex circuits 304, and the second layer of AIC 310 may be coupled between the MEMS based pMUT array 202 and the distal pMUT interposer 306. Further, the catheter handle connector 302 may pass ultrasound signals through the plurality of electronic flex circuits 304 to the distal end 108 of the ultrasonic catheter 100. Further, the catheter handle connector 302 may comprise board edge connectors (not shown) and connector pins (not shown) to pass the ultrasound signals towards the distal end 108 of the ultrasonic catheter 100.

Figure 4A:
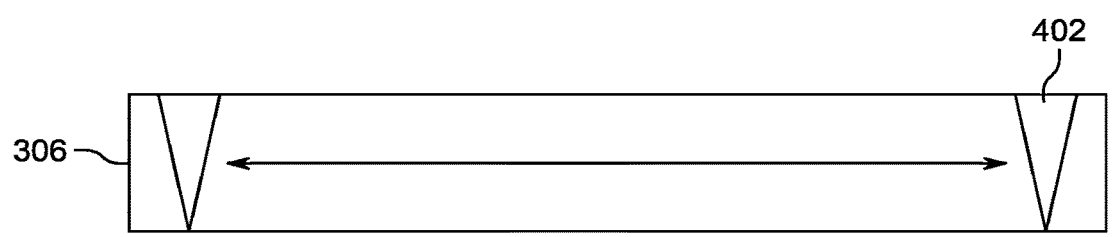
FIG. 4A illustrates a side view of InvisiVia or blind via connection shape, according to an embodiment of the present disclosure.

In one embodiment, the first layer of AIC 308 and the second layer of AIC 310 may provide a lead-free and environment friendly adhesive interconnect system. The first layer of AIC 308 and the second layer of AIC 310 may be used to create an electrically conductive adhesive bond for flexible and rigid circuits, as shown in FIG. 4A. Further, the first layer of AIC 308 and the second layer of AIC 310 may provide an extremely fine pitch capability for the pressure echo received from the MEMS based pMUT array 202.

Further, the distal pMUT interposer 306 sandwiched between the first layer of AIC 308 and the second layer of AIC 310, with InvisiVia connections 402, as shown in FIG. 4A. In one embodiment, the distal pMUT interposer 306 may be referred to as a distal PMUT flex cable interposer. Further, the distal pMUT interposer 306 may correspond to an ultra-high density (UHD) flexible circuit interposer connected to the MEMS based pMUT array 202 through a UHD interconnect pad (not shown). The UHD interconnect pad may be connected to the MEMS based pMUT array 202 through a use of near zero evidence interfacial via. In one embodiment, the first layer of the AIC 308 may provide connections between the plurality of electronic flex circuits 304 and the UHD interconnect pad. The second layer of the AIC 310 may provide connections between the UHD interconnect pad, and the MEMS based pMUT array 202.

It should be noted that the MEMS based pMUT array 202 may send a pressure wave and receive a returning pressure wave echo via the InvisiVia connections 402 of the distal pMUT interposer 306. Further, the use of the InvisiVia connections 402 may create a flat and planar interconnect with the UHD interconnect pad. In an example, the InvisiVia connections 402 creates a flat and planner interconnect diameter of not more than 5 um. Further, the InvisiVia connections 402 may be highly critical to an electrical performance of the ultrasonic catheter 100. In one embodiment, the InvisiVia connections 402 may eliminate a potential for undesired leakage to a bulk silicon substrate of the MEMS based pMUT array 202. In one embodiment, the InvisiVia connections 402 may be from 16 to 128.

Figure 4B:
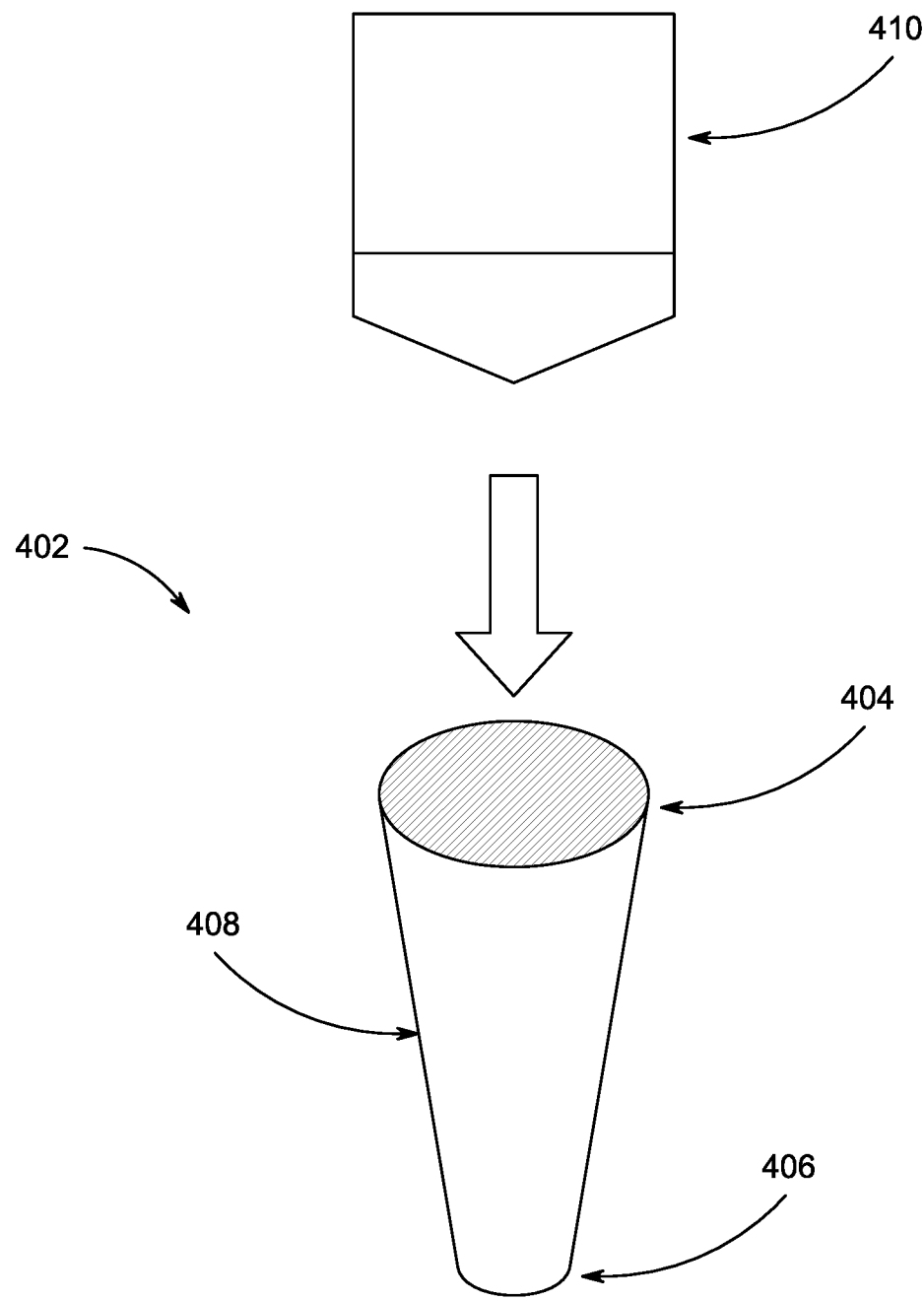
FIG. 4B illustrates the InvisiVia connection with a flat and planar interconnect from a flex circuitry to a highly planer attachment land/pad surface, according to an embodiment of the present disclosure.

Referring to FIG. 4B, the InvisiVia connection 402 with a flat and planar interconnect from a flex circuitry to a highly planer attachment land/pad surface, is disclosed, according to an embodiment of the present disclosure.

Figure 5:
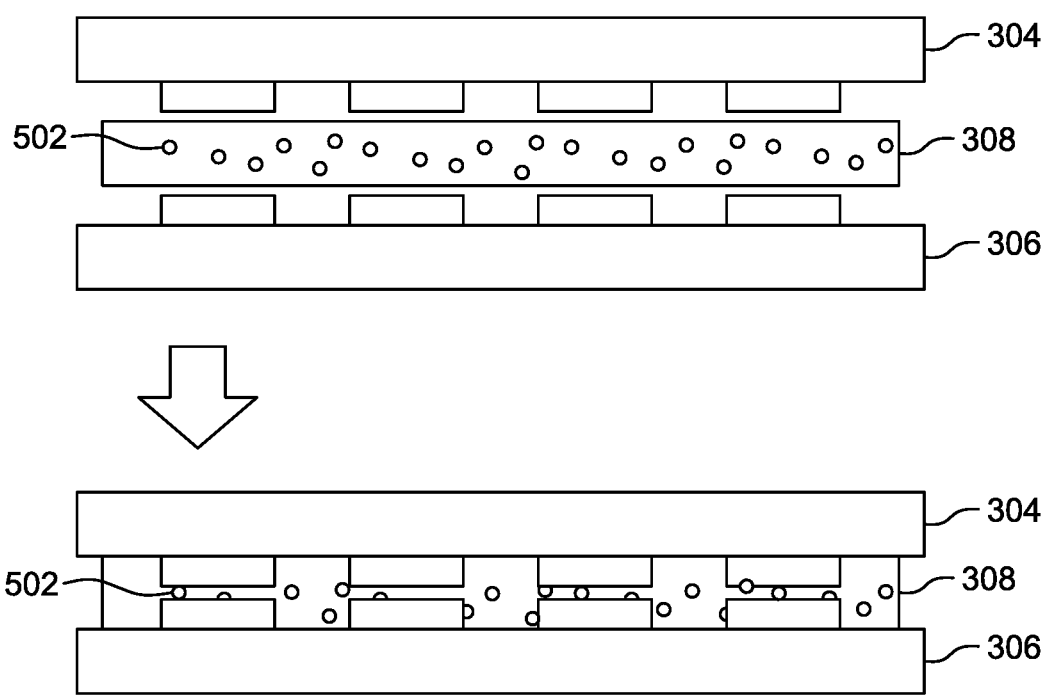
FIG. 5 illustrates a schematic diagram showing a first layer of AIC, connecting a plurality of electronic flex circuits to a distal pMUT interposer, according to an embodiment of the present disclosure.
Figure 6:
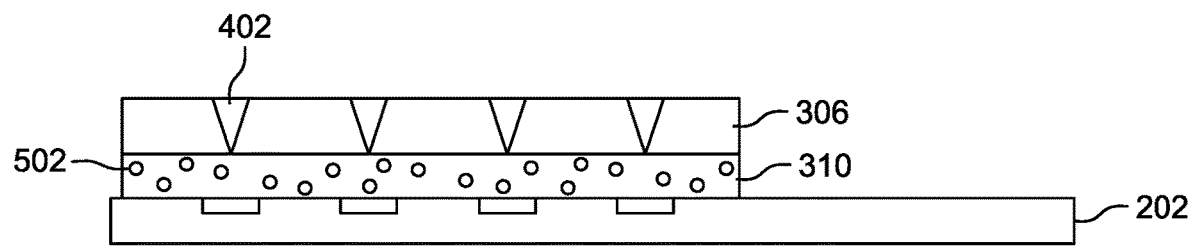
FIG. 6 illustrates an interconnect diagram showing a top view stackup of the InvisiVia connection to the MEMS based pMUT array through a second layer of AIC, according to an embodiment of the present disclosure.
Figure 6:
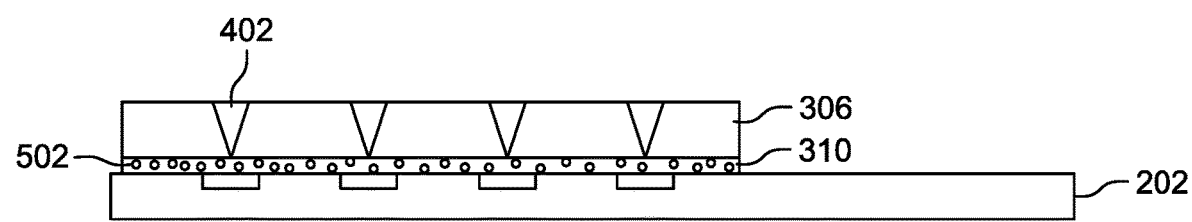

The InvisiVia connection 402 may be configured to bring the electronic flex circuit connections from one side of the distal pMUT interposer 306 to the other side. It can be noted that purpose of the InvisiVia connection 402 is that the second layer of AIC 310 should not connect to silicon disposed on side of the MEMS based pMUT array 202. Further, the InvisiVia connection 402 may create a flat and planar interconnect from the electronic flex circuit to second layer of AIC 310, as shown in FIGS. 5 and 6. In one embodiment, the flex bonding pads are electrically connected to the MEMS based pMUT array 202 utilizing a thermal compression adhesive system.

Figure 4C:
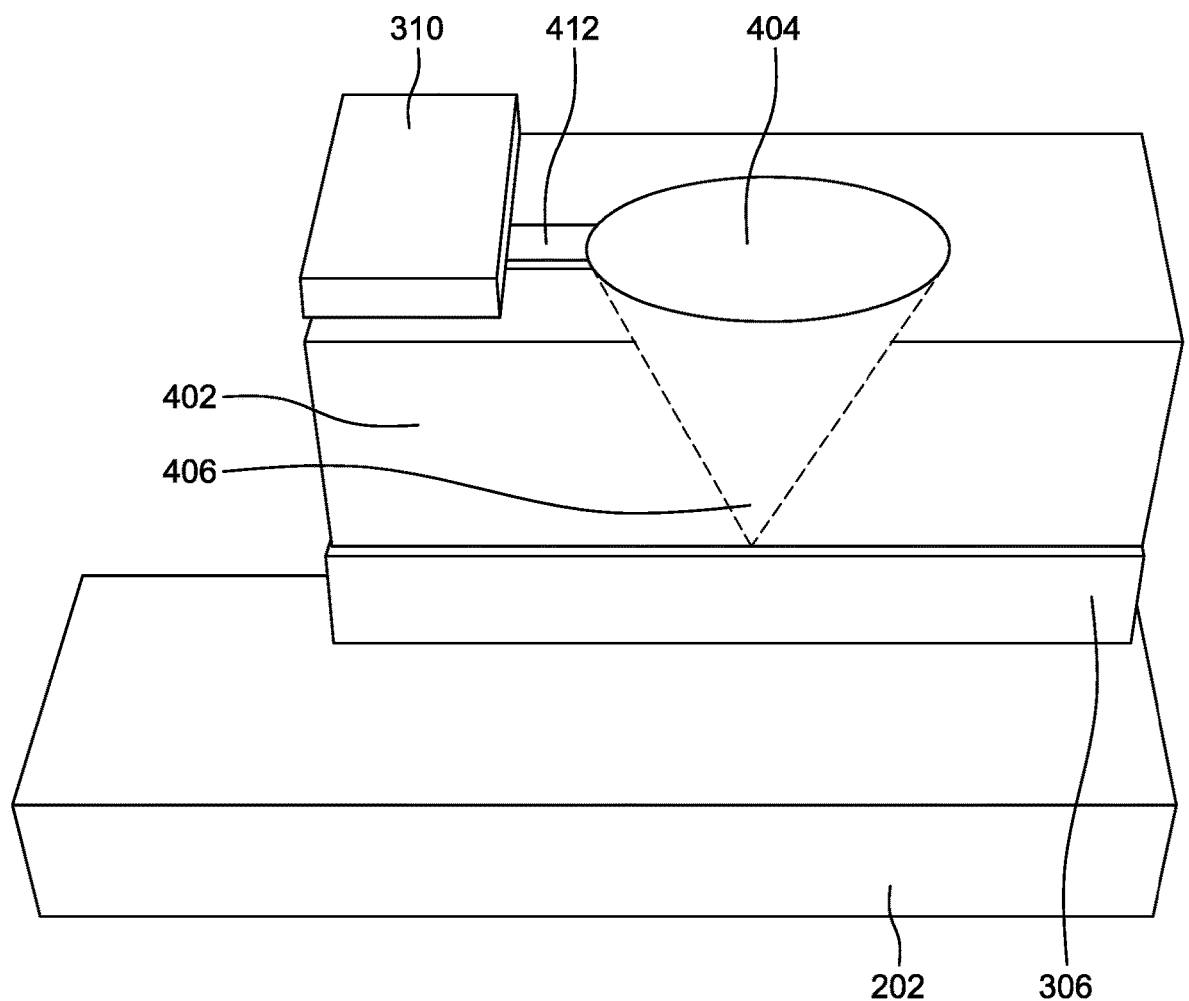
FIG. 4C illustrates a three-dimensional view with the InvisiVia connection disposed within the distal pMUT interposer, according to an embodiment of the present disclosure.

Further the InvisiVia connection 402 may be a conical section having a first end 404 and a second end. The InvisiVia connection 402 may be disposed within the distal pMUT interposer 306, as shown in FIG. 4C. The first end 404 and the second end 406 may have diameter ranging from 10 um to 25 um and 0 um to 8 um respectively. In one embodiment, the InvisiVia connection 402 is provided with an InvisiVia plating 408 between the first end 404 and the second end 406. In one embodiment, the first end 404 and the second end 406 may correspond to a top and bottom end of the InvisiVia connection 402. The first end 404 of the InvisiVia connection 402 may be connected to the second layer of AIC 310 via a trace 412. Further, the second end 406 of the InvisiVia connection 402 may connect through the second layer of AIC 310 to the MEMS based pMUT array 202. It can be noted that the InvisiVia connection 402 may facilitate the MEMS based pMUT array 202 with an extremely flat and planar surface with maximum surface area due to no or minimal copper penetration.

In one embodiment, the distal pMUT interposer 306 is aligned and bonded, and the pressure echo may be transmitted electrically through the InvisiVia connections 402 of the distal pMUT interposer 306. This provides for z-axis routing of the ultrasound signals from the MEMS based pMUT array 202. The first layer of AIC 308 and the second layer of AIC 310 may include a bonding material to physically hold the distal pMUT interposer 306 to the MEMS based pMUT array 202. The InvisiVia connections 402 may be created from a z-axis interconnect of two or more signals or ground layers utilizing an ultraviolet (UV) laser 410 with a hole diameter of no more than 10 um that is subsequently copper plating to a closed and highly planer attachment land/pad surface. In one embodiment, the UV laser 410 may have a beam width of less than 25 um.

FIG. 5 illustrates a schematic diagram showing the first layer of AIC 308, connecting the plurality of electronic flex circuits 304 to the distal pMUT interposer 306, according to an embodiment of the present disclosure.

Further, the distal pMUT interposer 306 may be coupled to the plurality of electronic flex circuits 304 via the first layer of AIC 308. The first layer of AIC 308 may comprise a plurality of conductive particles 502. It can be noted that the plurality of conductive particles 502 may create the compression connection between the plurality of electronic flex circuits 304 and the distal pMUT interposer 306. Therefore, a stable transmission of ultrasound signals is achieved by the first layer of AIC 308 between the plurality of electronic flex circuits 304 and the distal pMUT interposer 306. The first layer of AIC 308 may provide an extremely fine pitch capability for the pressure echo received from the MEMS based pMUT array 202.

FIG. 6 illustrates an interconnect diagram showing a top view stackup of the InvisiVia connection 402 to the MEMS based pMUT array 202 through the second layer of AIC 310, according to an embodiment of the present disclosure.

Further, the distal pMUT interposer 306 may be coupled to the MEMS based pMUT array 202 via the second layer of AIC 310, as shown in FIG. 6. It can be noted that the distal pMUT interposer 306 may create the compression connection between the InvisiVia connections 402 of the distal pMUT interposer 306 and the MEMS based pMUT array 202 via the plurality of conductive particle 502 of the second layer of AIC 310. It can also be noted that the second layer of AIC 310 may also provide the extremely fine pitch capability for the pressure echo received from the MEMS based pMUT array 202. In one embodiment, the InvisiVia connections 402 may create a flat and planner interconnect diameter of not more than 5 um.

Figure 7:
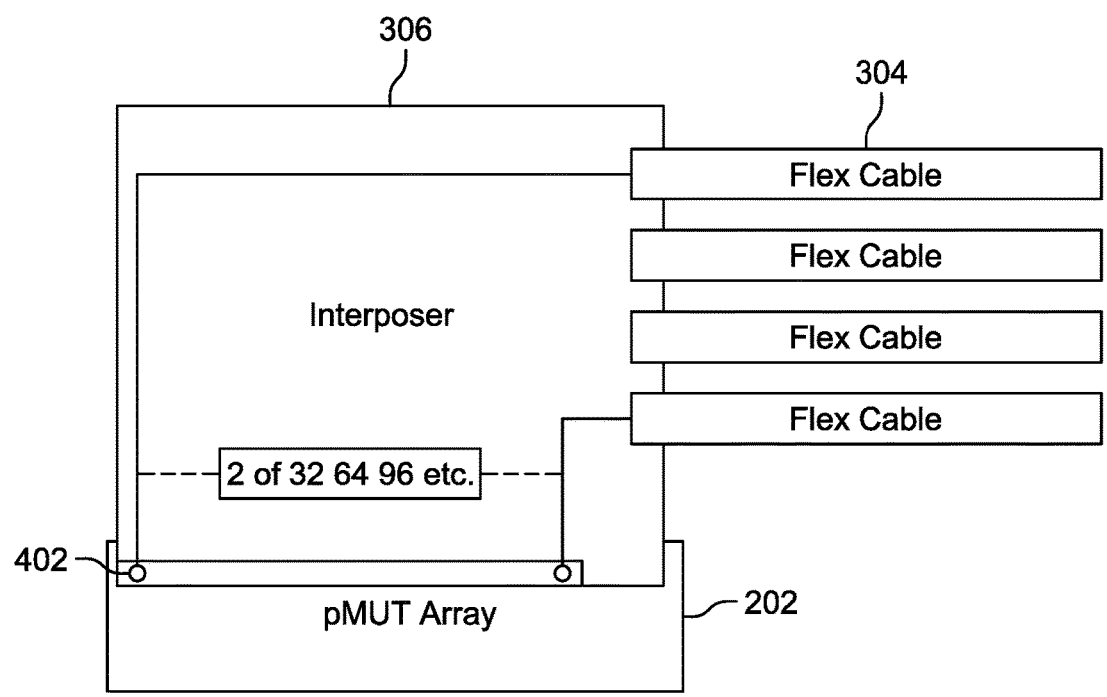
FIG. 7 illustrates a schematic diagram showing the AIC layer connecting the distal pMUT interposer to the MEMS based pMUT, according to an embodiment of the present disclosure.

FIG. 7 illustrates a schematic diagram showing the AIC layer connecting the distal pMUT interposer 306 to the MEMS based pMUT array 202, according to an embodiment of the present disclosure.

The plurality of electronic flex circuits 304 is connected to the distal pMUT interposer 306 via the first layer of AIC 308. The distal pMUT interposer 306 is connected to the MEMS based pMUT array 202 via the second layer of AIC 310. It can be noted that the distal pMUT interposer 306 may correspond to the UHD flexible circuit interposer connected to the MEMS based pMUT array 202 through an UHD interconnect pad. The UHD interconnect pad may be connected to the MEMS based the pMUT array 202 through a use of near zero evidence interfacial via. Further, the use of InvisiVia connections 402 may create the flat and planner interconnect with the MEMS based pMUT array 202. Further, the compression connections may be made between the plurality of electronic flex circuits 304, the first layer of AIC 308, the distal pMUT interposer 306, the second layer of AIC 310, and the MEMS based pMUT array 202. In one embodiment, the use of InvisiVia connections 402 may eliminate a potential for undesired leakage to bulk silicon substrate of the MEMS based pMUT array 202.

Figure 8:
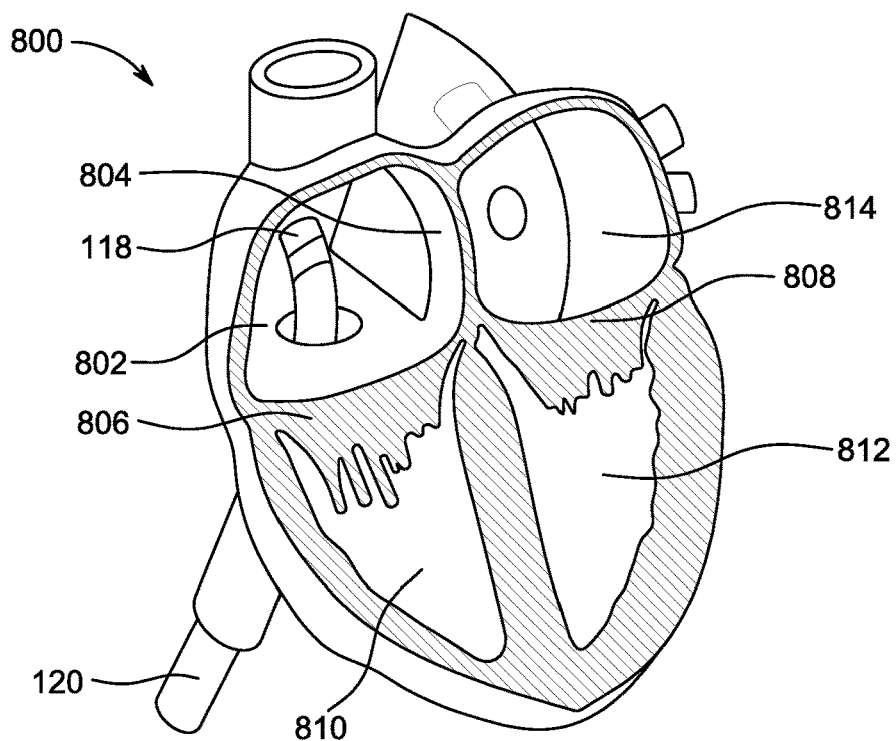
FIGS. 8-9 illustrate cross sectional images of a heart with the ultrasonic catheter positioned within a right atrium of the heart, according to an embodiment of the present disclosure.
Figure 9:
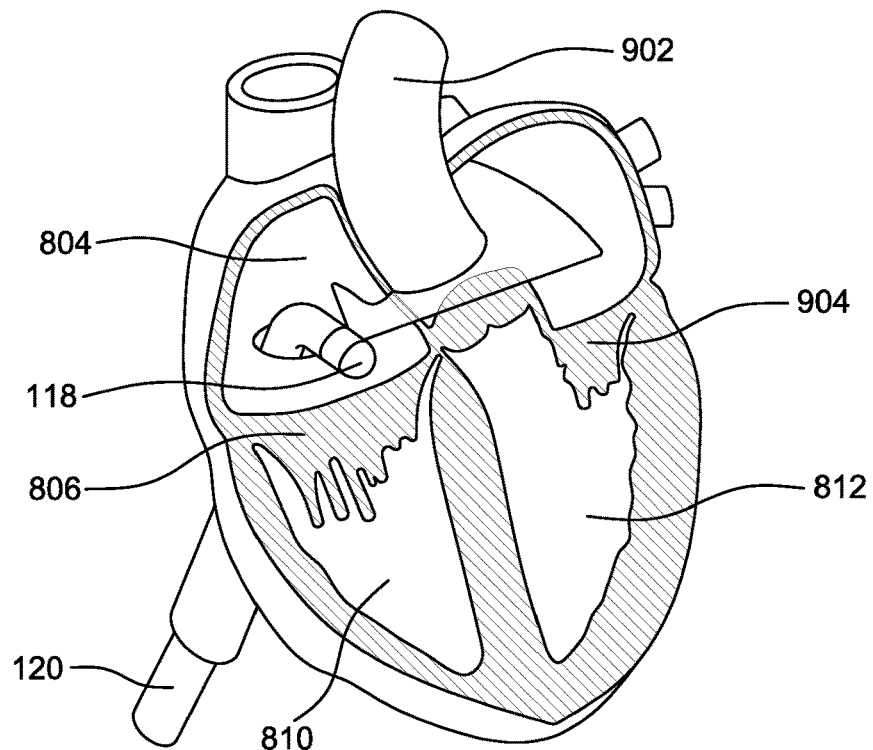

Referring to FIGS. 8-9, cross sectional images of a heart 800 with the ultrasonic catheter 100 positioned within a right atrium 802 of the heart 800, are disclosed. The distal tip 118 of the ultrasonic catheter 100 may be inserted into the right atrium 802 via an inferior vena cava (not shown). In order to perform an adequate imaging of an interatrial septum (IAS) 804 and its neighbouring structures, two standardized views may be used. The movement of the distal tip 118 of the ultrasonic catheter 100 within the right atrium 802 may be controlled by the steering control unit 112. Further, the movement of the distal tip 118 by the steering control unit 112 clockwise or counterclockwise, may allow the imaging window to move from posterior view to anterior view or vice versa.

Further, as shown FIGS. 8-9, to properly place the MEMS based pMUT array 202 into position for imaging the right atrium 802 and a bicuspid valve 806, the flexible sheath may be introduced into the patient's vascular structure via a femoral vein (not shown). Using a fluoroscopic imaging to monitor the ultrasonic catheter's position, a clinician may advance the distal end 108 of the ultrasonic catheter 100 into the right atrium 802. In order to guide the ultrasonic catheter 100 through turns in the patient's vascular structure, the clinician may rotate the distal tip 118 clockwise or counterclockwise to allow the imaging window to move towards from the anterior position to the posterior position and vice versa. Once the distal tip 118 of the ultrasonic catheter 100 is in the right atrium 802, the clinician may rotate the distal tip 118 so as to introduce an acute bend in the flexible sheath to direct the MEMS based pMUT array 202 through a tricuspid valve 808 and into a right ventricle 810, as shown in FIG. 6. In this position, a field of view of the MEMS based pMUT array 202 may include portions of the right ventricle 810, the IAS 804, the bicuspid valve 806, a left ventricle 812, a left atrium 814 and a left ventricular wall. In one embodiment, when the MEMS based pMUT array 202 is directed clockwise, the right ventricle 810 and right ventricular wall may be imaged. It can be noted that the clinician may twist the ultrasonic catheter 100, while positioned within the heart 800 as illustrated in FIGS. 8-9, the MEMS based pMUT array 202 may swing about an axis, which could injure the tricuspid valve 808 or cause the MEMS based pMUT array 202 to strike the IAS 804. FIG. 8 shows a perpendicular short-axis view to visualize interior parts of the IAS 804. The interior parts of the IAS 804 include an aorta 902, a mitral valve 904 towards the left ventricle 812.

In one exemplary embodiment, the standard view is obtained by placing the ultrasonic catheter 100 in a mid-right atrium and the MEMS based pMUT array 202 in a neutral position facing the tricuspid valve 808. The standard view provides imaging of the right atrium 802, the tricuspid valve 808, the right ventricle 810, and typically an oblique or short-axis view of the aortic valve.

Further, when the ultrasonic catheter 100 may be rotated clockwise the aortic valve in long axis and the right ventricle 810 outflow tract is viewed. In this view, the tricuspid valve 808 that is closer to the MEMS based pMUT array 202 or the distal tip 118 is a non-coronary cusp, which is in close relationship to a membranous septum and a para-hisian region, whereas the opposite is a right coronary cusp, which is the most anterior of the aortic cusps, directly posterior to the right ventricle 810 outflow tract infundibulum and pulmonic valve. The left ventricle 812 is visualized anterior to the most septal portion of the right atrium 802, and the opening of the coronary sinus becomes evident. In this view, the long axis of the left ventricle 812 outflow tract is identified, and the posterior left ventricle 812 is in view just below the non-coronary cusp.

Further, an additional clockwise rotation of the ultrasonic catheter 100 allows visualization of the mitral valve 904 and the IAS 804, with the left atrial appendage anteriorly and the coronary sinus posteriorly. The left atrium 814 appendage is examined for the presence of thrombus at its ostium, and mitral regurgitation may be assessed using a colour Doppler.

In one embodiment, most catheters used in intravascular applications, particularly those with ultrasound transducers, are at least about 6 French in diameter. The electronics and wires needed for ultrasound transducer arrays have made it impractical and expensive to reduce the size of such catheters below about 6 French. Nevertheless, there are benefits in reducing the diameter of the catheter, and technology advances may enable the electronics and control structures to be further reduced in size. The bundling arrangement of the coaxial cables, steering and pivot cables and steering and pivot mechanisms described in more detail below, make it possible to effectively reduce the diameter below about 6 French, to about 5 French, about 4 French, about 3 French, or even about 2 French.

While there is shown and described herein certain specific structures embodying various embodiments of the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An ultrasonic catheter comprising:
  a body having a longitudinal axis, a proximal end, and a distal end;
  a micro-electromechanical (MEMS) based Piezoelectric Micromachined Ultrasonic Transducer (pMUT) array disposed within the distal end of the body;
  a plurality of electronic flex circuits, connected at one end to a handle connector and at other end to a first layer of Adhesive Interconnect (AIC), wherein the handle connector passes ultrasound signals to the distal end via the plurality of electronic flex circuits; and
  a distal pMUT interposer disposed between the first layer and a second layer of AIC, with InvisiVia connections, wherein the InvisiVia connections are configured to bring the electronic flex circuit from one side of the distal pMUT interposer to the other,
  wherein the MEMS based pMUT array sends a pressure wave and receives a returning pressure wave echo via the InvisiVia connections of the distal pMUT interposer.

2. The ultrasonic catheter of claim 1, wherein a compression connection is made among the plurality of electronic flex circuits, the first layer of AIC, the distal pMUT interposer, the second layer of AIC, and the MEMS based pMUT array, using the AIC.

3. The ultrasonic catheter of claim 1, wherein the distal pMUT interposer corresponds to an ultra-high density (UHD) flexible circuit interposer connected to the MEMS based pMUT array through an ultra-high density (UHD) interconnect pad.

4. The ultrasonic catheter of claim 3, wherein the UHD interconnect pad is connected to the MEMS based pMUT array through a use of near zero evidence interfacial via.

5. The ultrasonic catheter of claim 1, wherein the InvisiVia connections provide connections between the first and second layers of AIC.

6. The ultrasonic catheter of claim 3, wherein the first layer of the AIC provides connections between the plurality of electronic flex circuits and the UHD interconnect pad.

7. The ultrasonic catheter of claim 3, wherein the second layer of the AIC provides connections between the UHD interconnect pad, and the MEMS based pMUT array.

8. The ultrasonic catheter of claim 4, wherein the use of InvisiVia connections creates a flat and planner interconnect with the UHD interconnect pad.

9. The ultrasonic catheter of claim 1, wherein the InvisiVia connections creates a flat and planner interconnect diameter of not more than 5 um.

10. The ultrasonic catheter of claim 1, wherein the use of InvisiVia connections eliminates a potential for undesired leakage to bulk silicon substrate of the MEMS based pMUT array.

11. The ultrasonic catheter of claim 1, wherein the InvisiVia connections provide an extremely flat and planar surface with maximum surface area due to minimal copper penetration.

12. The ultrasonic catheter of claim 1, wherein the InvisiVia connections are between 30 to 128 in number.

13. The ultrasonic catheter of claim 1, wherein each of the InvisiVia connections is created from a z-axis interconnect of two or more signals or ground layers utilizing an ultraviolet (UV) laser with a hole diameter of no more than 10 um that is subsequently copper plating to a closed and highly planer attachment land/pad surface.

14. The ultrasonic catheter of claim 1, wherein each of the InvisiVia connections has a first end and a second end, with diameters ranges of 5 μm to 25 μm and 0 μm to 10 um respectively.

15. The ultrasonic catheter of claim 14, wherein each of the InvisiVia connections is provided with an InvisiVia plating between the first end and the second end.

16. The ultrasonic catheter of claim 1, wherein the MEMS based pMUT array comprises a plurality of MEMS based pMUT array elements.

17. The ultrasonic catheter of claim 16, wherein each of the plurality of MEMS based pMUT array elements is a linear phased array.

18. The ultrasonic catheter of claim 16, wherein the plurality of MEMS based pMUT array elements creates an individual focused beam.

* * * * *